(12) United States Patent
Jaakkola

(10) Patent No.: US 10,215,681 B2
(45) Date of Patent: Feb. 26, 2019

(54) SYSTEM FOR ELIMINATING ELECTRICALLY CONDUCTIVE PARTICLES

(71) Applicant: Ilkka Jaakkola, Karhe (FI)

(72) Inventor: Ilkka Jaakkola, Karhe (FI)

( * ) Notice: Subject to any disclaimer, the term of this patent is extended or adjusted under 35 U.S.C. 154(b) by 288 days.

(21) Appl. No.: 15/112,025

(22) PCT Filed: Dec. 23, 2014

(86) PCT No.: PCT/FI2014/051050
§ 371 (c)(1),
(2) Date: Jul. 15, 2016

(87) PCT Pub. No.: WO2015/114199
PCT Pub. Date: Aug. 6, 2015

(65) Prior Publication Data
US 2016/0349169 A1 Dec. 1, 2016

(30) Foreign Application Priority Data

Jan. 29, 2014 (FI) ..................................... 20145095

(51) Int. Cl.
*G01N 33/28* (2006.01)
*G01N 15/10* (2006.01)
(Continued)

(52) U.S. Cl.
CPC ........... *G01N 15/1031* (2013.01); *B03C 3/72* (2013.01); *B03C 5/02* (2013.01); *G01N 33/2858* (2013.01); *F01N 3/0275* (2013.01)

(58) Field of Classification Search
CPC ........... G01N 15/1031; G01N 33/2858; G01N 33/28; B03C 3/72; B03C 5/02;
(Continued)

(56) References Cited

U.S. PATENT DOCUMENTS

| 3,193,815 A | 7/1965 | Prestel |
| 4,070,660 A | 1/1978 | Tauber |

(Continued)

FOREIGN PATENT DOCUMENTS

| DE | 3804779 A1 | 10/1988 |
| EP | 0730144 A2 | 9/1996 |

(Continued)

OTHER PUBLICATIONS

PCT/ISA/210—International Search Report—dated May 25, 2015 (Issued in Application No. PCT/FI2014/051050).

(Continued)

*Primary Examiner* — Walter D. Griffin
*Assistant Examiner* — Cameron J Allen
(74) *Attorney, Agent, or Firm* — Venable LLP; Jeffri A. Kaminski

(57) ABSTRACT

A system for eliminating electrically conductive particles by detecting and destroying electrically conductive particles in a medium circulation. Electrodes are arranged by a power supply in potentials differing from each other, whereby electrically conductive particles getting drifted in connection therewith are arranged to be detected and destroyed by causing a shortcut between the electrodes. A device having a uniform frame. Inside the device there is a flow space for a flow-through of a medium circulation occurring inside thereof in its longitudinal direction. The flow space has, when viewed in a crosswise plane perpendicular to its longitudinal direction, adjacent narrow flow ways in one or more directions. Opposite walls of the flow ways are arranged as electrodes in potentials differing from each other.

13 Claims, 4 Drawing Sheets

(51) Int. Cl.
  *B03C 3/72* (2006.01)
  *B03C 5/02* (2006.01)
  *F01N 3/027* (2006.01)
(58) Field of Classification Search
  CPC . B03C 3/00; F01N 3/0275; F01N 3/00; F01N 3/01; F01N 3/38; H01T 19/00; H01T 19/04; F02B 3/00; F02B 3/06; F02B 1/04; F02B 1/00
  See application file for complete search history.

(56) References Cited

U.S. PATENT DOCUMENTS

| | | | |
|---|---|---|---|
| 4,283,207 A | | 8/1981 | Martyniuk |
| 4,376,637 A | * | 3/1983 | Yang .................. B03C 3/00 422/121 |
| 4,852,349 A | | 8/1989 | Abthoff et al. |
| 6,664,492 B1 | | 12/2003 | Babb et al. |

FOREIGN PATENT DOCUMENTS

| | | |
|---|---|---|
| FR | 2884857 A1 | 10/2006 |
| FR | 2915234 A1 | 10/2008 |

OTHER PUBLICATIONS

PCT/ISA/237—Written Opinion of the International Searching Authority—dated May 25, 2015 (Issued in Application No. PCT/FI2014/051050).

Supplementary European Search Report dated Oct. 4, 2017, in corresponding European Application No. 14881138.3 (2 pages).

* cited by examiner

SYSTEM FOR ELIMINATING ELECTRICALLY CONDUCTIVE PARTICLES

CROSS-REFERENCE TO RELATED APPLICATIONS

The application claims priority to Finnish patent application 20145095 filed 29 Jan. 2014 and is the national phase under 35 U.S.C. § 371 of PCT/FI2014/051050 filed 23 Dec. 2014.

FIELD OF THE INVENTION

The invention relates to a system for eliminating electrically conductive particles and it is meant to detect and destroy electrically conductive particles in a medium circulation. The system comprises electrodes that are arranged by means of power supply means in potentials differing from each other, whereby electrically conductive particles getting drifted in connection therewith are arranged to be detected and destroyed by causing a shortcut between the electrodes.

BACKGROUND OF THE INVENTION

There is a need for the above described systems in e.g. different kinds of machines with fluid circulation, such as engines, bearings, gearings, clutches etc., because in a fluid circulation, due to wear of e.g. the machine or the machinery in connection with it or due to a mechanical malfunction, metal particles get drifted into the fluid circulation always harming the functioning of the machine and at worst even causing a risk of breakdown. This causes significant expenses especially in connection with expensive and massive machines. In order to eliminate the above mentioned problem, a system has been presented e.g. in the published application EP 0730144. With this kind of system it is possible both to detect and to destroy electric particles in a fluid circulation when the particles touch the electrodes of the electric detectors in the system. The solution in question is carried out advantageously with automation in a microprocessor operated manner by utilizing one or more electric circuits separate from each other in the use of different detectors, wherein an electric particle that has caused a shortcut in the detector is combusted by a higher shortcut current, being led to the detector by a condenser arrangement.

The solution described above is especially meant as an integrated system e.g. in connection with aero engines or the like, wherein the electric detectors together with the electrodes thereof are placed in suitable points in the fluid circulation of the engine.

Also in patent publication U.S. Pat. No. 4,070,660 there has been presented a solution executed in the same manner as the solution explained here above for detecting and, if possible, for eliminating electric particles in a fluid circulation. This solution is carried out e.g. with a plug provided in connection with the fluid circulation, which plug is equipped in addition to electrodes with a permanent magnet in order to pull the metallic particles in the fluid circulation magnetically to itself. Utilizing a magnetic field is not relevant from the point of view of the elimination of the metallic particles, because they "get locked" into the electrodes in a shortcut situation. Also in this solution, it is possible to couple the plugs to be installed in different points in the fluid circulation electrically in parallel in different electric circuits, wherein functioning of each plug is independent from other plugs. The problem in this solution is that the prerequisite of good functioning is first of all an optimal placement of the plugs, because with "erroneously" placed plugs, a reliable detection or removal of the metal particles from the fluid circulation can not be ensured. On the other hand this solution has a limited operation efficiency, because it enables removal of magnetic particles only, whereas all other electrically conductive harmful particles remain undetected and unremoved.

Despite the above mentioned solutions, the situation regarding the technical problem described in the beginning still prevails, so that there does not exist a system for eliminating electrically conductive particles from fluid circulation e.g. in connection with the most varied kinds of fluid circulation machines and apparatuses on the market that would be both sufficiently simple to execute as well as both reliable and affordable.

SUMMARY

It is an aim of the system according to the present invention to achieve a decisive improvement in the problems described above and thus to raise essentially the level of prior art.

As the most important advantages of the system according to the invention may be mentioned the simplicity and efficiency of the device configurations applicable for the same, whereby detection and eliminating of the most varied kinds of electrically conductive particles is enabled on the same principle in the most varied medium circulation operated apparatuses. The most important advantage of the present invention is first of all in that that the medium circulation being monitored at any given time is arranged as a whole to take place as a flow-through through parallel and narrow flow channels in the flow space of the device, wherein the electrically conductive particles cause a shortcut as they connect the opposite walls of the flow channels. The system according to the invention furthermore enables easy installation thereof as a complete device entirety e.g. in connection with the fluid circulation operated apparatus to be monitored at any given time in a way that e.g. by using two devices coupled in parallel, it is furthermore possible to ensure the continuous operation of the fluid circulation apparatus e.g. when one of the devices has stopped functioning or while being under maintenance.

Other advantageous embodiments of the system according to the invention have been described herein.

BRIEF DESCRIPTION OF THE DRAWINGS

In the following description, the invention is illustrated in detail with reference to the appended drawings, in which in FIG. 1 is shown a cross section of a device belonging to the system according to the invention in a direction perpendicular to the medium circulation taking place through the device, in FIG. 2 is shown a cross section perpendicular to the view shown in FIG. 1 of an inner part of the device, in FIG. 3 is shown in detail an advantageous way of executing the walls of the flow channels in the flow space, and in FIG. 4 is shown an advantageous general operating principle of the system according to the invention.

DETAILED DESCRIPTION OF EMBODIMENTS OF THE INVENTION

The invention relates to a system for eliminating electrically conductive particles, the system being meant to detect and destroy electrically conductive particles in a medium circulation. The system comprises electrodes E that are arranged by means of power supply means V in potentials differing from each other, whereby electrically conductive particles getting drifted in connection therewith are arranged to be detected and destroyed by causing a shortcut between the electrodes. Especially with reference to the advantageous embodiment shown in FIGS. 1 and 2, the system comprises a device L having a uniform frame 1, wherein inside the device there is a flow space 2 for a flow-through of a medium circulation occurring inside thereof in its longitudinal direction, which flow space has, when viewed according to FIG. 1 in a crosswise plane perpendicular to its longitudinal direction, adjacent narrow flow ways 3 in one or more directions, wherein opposite walls 3a, 3a' of the flow ways are arranged as electrodes E in potentials differing from each other.

As an advantageous embodiment of the system according to the invention, the power supply means V, advantageously being provided with a fuse arrangement, are arranged operable by a low-voltage power source and provided with an auxiliary power arrangement, such as a supplementary power supply coupling LK, condenser coupling and/or a like, in order to produce a higher current needed for destroying a particle that has caused a shortcut situation.

As a furthermore advantageous embodiment of the system according to the invention, a flow space 2 formed of narrow flow ways 3 consists of, when viewed in its cross section, two or more flow zones VZ1, VZ2, VZ3 coupled in separate electric circuits in order to process shortcut situations occurring in each flow zone independently with respect to each other. The multiple zoned execution of the flow space is advantageous first of all thanks to the fact that it enables a better monitoring of the "general condition" of the circulating medium, being explained in detail later on.

Figure 1:
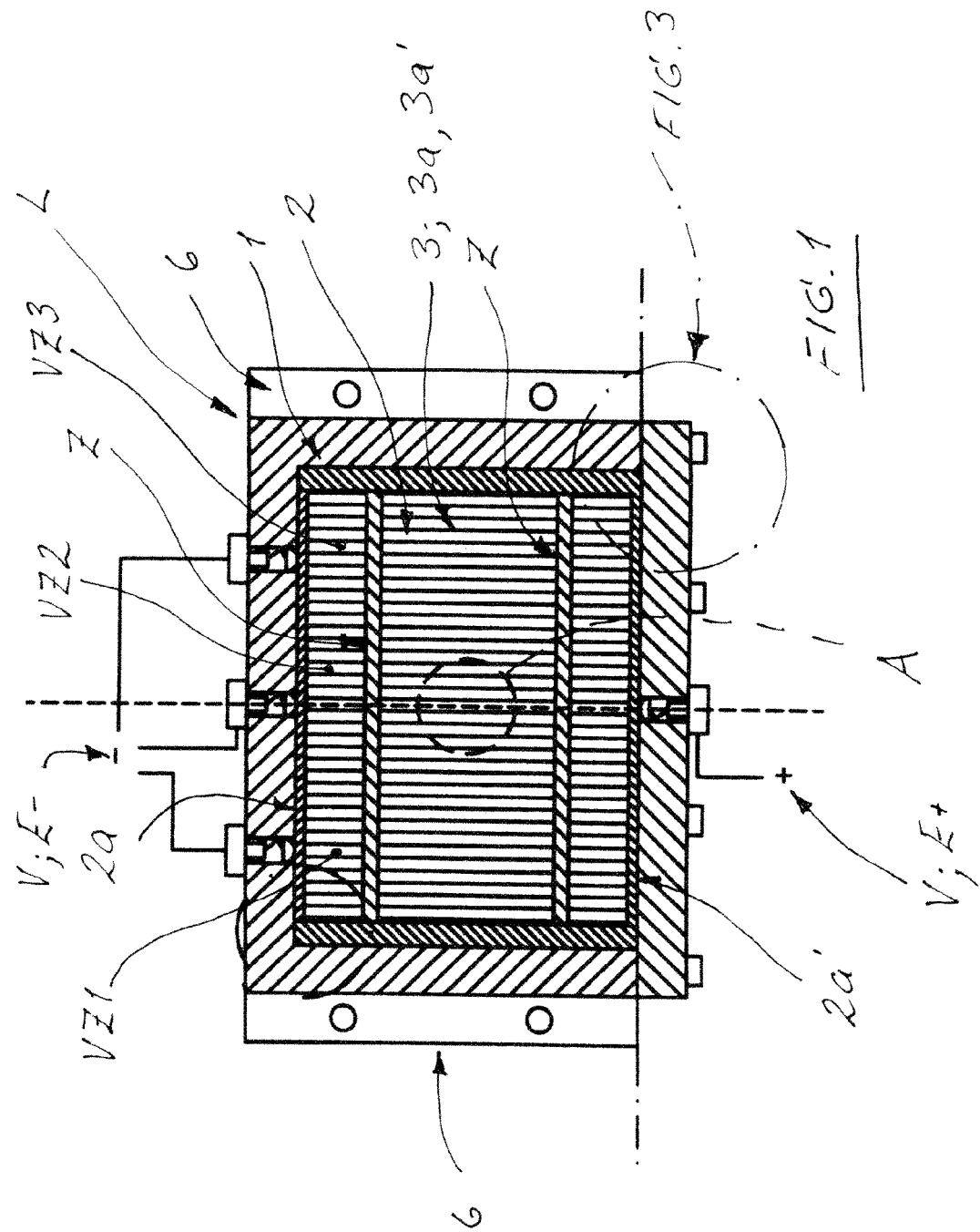
Figure 2:
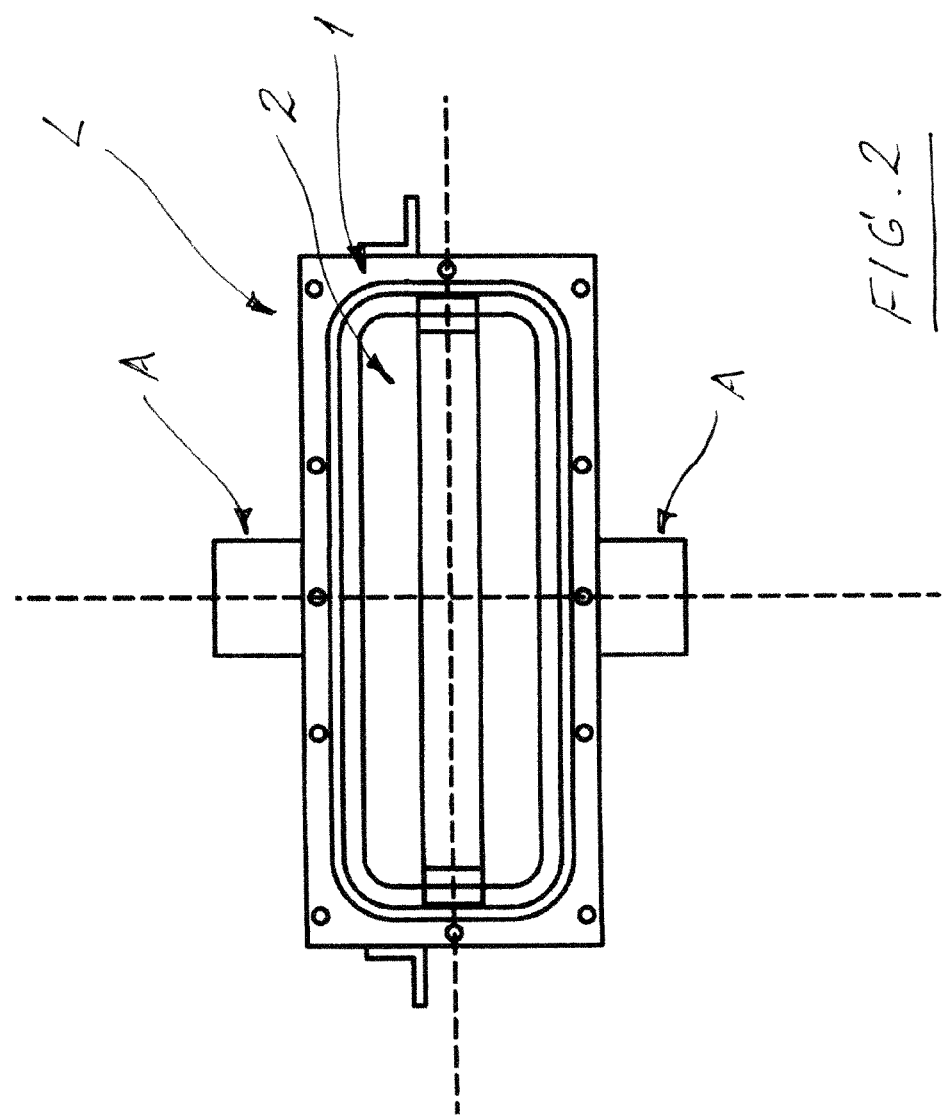

Furthermore as an advantageous embodiment of the system according to the invention, especially with reference to the general operating principle shown in FIG. 1, the system comprises a programmable logic 4, such as one or more microprocessors, logic circuits and/or alike, for automatic independent functioning of the system.

Figure 4:
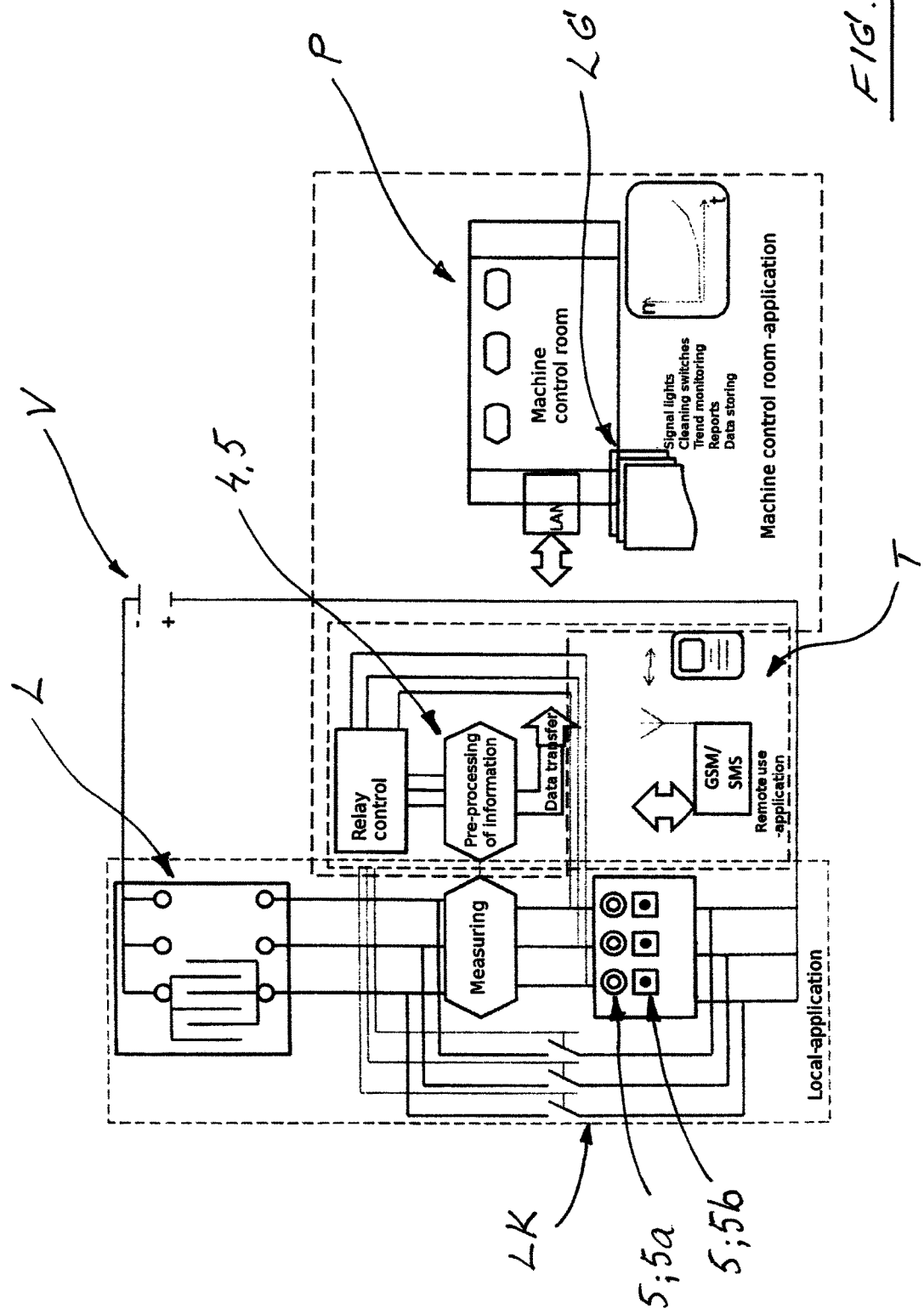

As a furthermore advantageous embodiment of the system according to the invention, it is provided with monitoring means 5 for monitoring of the functioning and use of the system on the principle shown in FIG. 4 by means of local voice-operated, light-operated 5a and/or the like detectors.

Furthermore with reference to the general operating principle shown in FIG. 4, a manual supplementary power supply coupling LK has been utilized therein, wherein, when the signal lamp 5a has indicated that a shortcut has occurred, by pressing the push button 5b, supplementary power will be supplied by parallel feed of electric current, being generated in a relay controlled manner, in order to destroy the particle by combustion. In case it is a small particle, it can be eliminated automatically by the "basic current" of the electric circuit.

As a furthermore advantageous embodiment of the system according to the invention, monitoring information from the monitoring means 5 is transmitted through a wired connection in order to enable use and control of the system on remote control principle P e.g. as shown in FIG. 4 from a machine control room. In this context, as a furthermore advantageous embodiment of the system according to the invention, use and control of the system is arranged wirelessly T, such as by a control software operating on cloud server principle by applying a mobile telephone network, Internet and/or the like.

Furthermore as an advantageous embodiment of the system according to the invention, the monitoring means 5 are provided with a logging function LG in order to monitor development of a shortcut frequency detected in the flow space's one or more flow zones VZ1, VZ2, VZ3. An increase in malicious particles usually signals that some part in the process is getting broken, wherein the system according to the invention enables e.g. the check up and maintenance on the components of the fluid circulation process well in time, thanks to which further damages may be avoided.

When using multiple electrically separate flow zones, shortcut situations occurring more frequently in multiple flow zones is also a signal of the need for maintenance.

Furthermore as an advantageous embodiment of the system according to the invention, the frame 1 of the device L, being provided with flow couplings A, is provided with fastening means 6 for the coupling of the device removably with the medium circulation to be monitored.

Furthermore as an advantageous embodiment of the system according to the invention, it comprises at least two devices L to be coupled in parallel within the medium circulation to be monitored in order to make sure uninterrupted functioning of the circulation process in question. In this way, a most uninterrupted functioning of the process in question is made possible, because the devices according to the invention may be serviced or replaced by another when needed etc.

Figure 3:
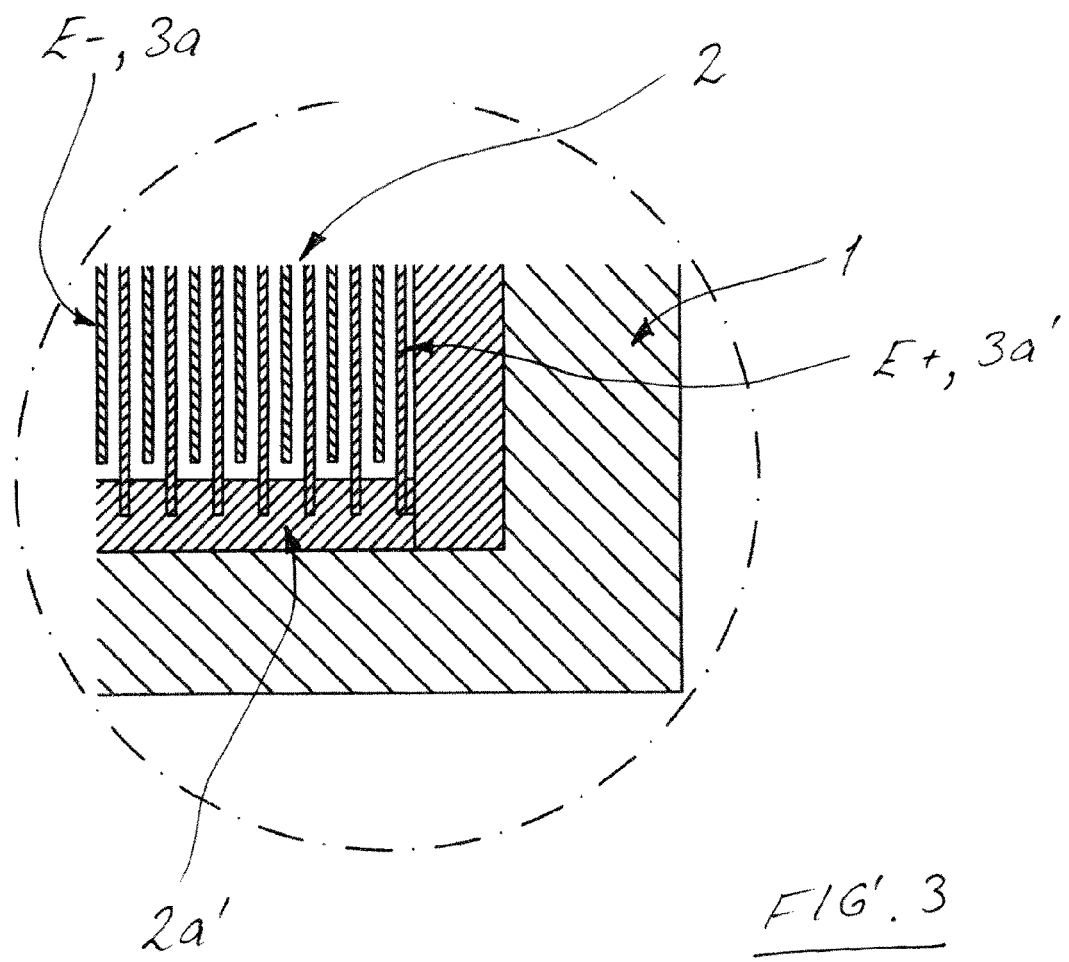

Especially with reference to FIGS. 1 and 3, every other wall 3a' of the flow channels 3 in the flow space 2 is coupled to the flow space's wall 2a' being coupled to the positive pole of the power source. At the opposite ends of these walls, there remains an air gap between the walls and the opposite wall 2a of the flow space. The rest of the walls 3a of the flow channels in the flow space are coupled to three different electric circuits connected to the negative pole of the power source, wherein the flow zones VZ1, VZ2, VZ3 are formed from walls being coupled to the opposite wall 2a of the flow space that comprises three structural parts being isolated from each other. The walls 3a, 3a' are being kept separate by support ribs Z.

The width of the flow channels in the flow space is arranged to suit the needs of the medium circulation process being monitored at any given time, wherein, at smallest, the width thereof may be even a tenth of a millimeter. Respectively, as for the power supply, e.g. a 12/24 V low current source is advantageously used as the power source, wherein the maximum current of the power circuit of each flow zone is limited by a fuse arrangement to e.g. 20 A. The electric power of the system according to the invention is typically between 0.75-1.5 kW, wherein a sufficient power in most usual applications in practice is about 1 kW.

It is clear that the invention is not limited to the embodiments shown or described here above, but it can be modified within the basic idea of the invention in very many ways e.g. by varying the cross sectional shapes and structures shown in the drawings according to the need at any given time. The system according to the invention may be exploited in connection with the most different types of medium circulation processes, wherein the circulation medium being monitored may be e.g. lubricant, liquid coolant, or the like, or water, air, steam or some other gas.

The invention claimed is:
1. A system for eliminating electrically conductive particles by detecting and destroying electrically conductive particles in a medium circulation, the system comprising:
   a device having a uniform frame, a flow space inside the device for a flow-through of a medium circulation occurring inside thereof in a longitudinal direction of the flow space, the flow space comprises, when viewed in a crosswise plane perpendicular to the longitudinal direction, adjacent narrow flow ways in at least one direction, wherein opposite walls of the flow ways are arranged by a power supply as electrodes in potentials differing from each other, whereby electrically conductive particles getting drifted in connection therewith are arranged to be detected and destroyed by causing a shortcut between the electrodes, wherein the flow space formed of narrow flow ways comprises, when viewed in its cross section, at least two flow zones coupled in separate electric circuits in order to process shortcut situations occurring in each flow zone independently with respect to each other.

2. The system according to claim 1, wherein the power supply is arranged operable by a low-voltage power source and comprises an auxiliary power arrangement in order to produce a higher current needed for destroying a particle that has caused a shortcut situation.

3. The system according to claim 1, further comprising: a programmable logic for automatic independent functioning of the system.

4. The system according to claim 1, further comprising: a monitor configured to monitor functioning and use of the system, the monitor comprising local voice-operated, light-operated detectors.

5. The system according to claim 4, wherein monitoring information from the monitor is transmitted through a wired connection in order to enable remote use and control of the system.

6. The system according to claim 1, wherein use and control of the system is arranged wirelessly.

7. The system according to claim 4, wherein the monitor comprises a logging function in order to monitor development of a shortcut frequency detected in the at least one flow zone of the flow space.

8. The system according to claim 1, wherein the frame of the device comprises flow couplings and a fastener configured to removably couple the device with the medium circulation to be monitored.

9. The system according to claim 1, wherein the system comprises at least two devices to be coupled in parallel within the medium circulation to be monitored in order to make sure uninterrupted functioning of the circulation process in question.

10. The system according to claim 2, wherein the power supply comprises a fuse arrangement, and the auxiliary power arrangement comprises at least one of a supplementary power supply coupling or a condenser coupling.

11. The system according to claim 3, wherein the programmable logic comprises at least one of at least one microprocessor or logic circuit.

12. The system according to claim 6, wherein use and control of the system is arranged wirelessly by a control software operating on cloud server principle by applying at least one of a mobile telephone network or the internet.

13. A method for eliminating electrically conductive particles, the method comprising:
    directing the medium circulation through a flow space inside the device in a longitudinal direction of the flow space, wherein the flow space comprises, when viewed in a crosswise plane perpendicular to its the longitudinal direction, adjacent narrow flow ways in at least one direction, wherein opposite walls of the flow ways are arranged by a power supply as electrodes in potentials differing from each other; and
    detecting and destroying conductive particles drifted in connection with the electrodes by causing a shortcut between the electrodes, wherein the flow space formed of narrow flow ways comprises, when viewed in its cross section, at least two flow zones coupled in separate electric circuits in order to process shortcut situations occurring in each flow zone independently with respect to each other.

* * * * *